United States Patent
Wang et al.

(10) Patent No.: US 7,507,199 B2
(45) Date of Patent: *Mar. 24, 2009

(54) METHOD AND APPARATUS FOR PERFORMING MINIMALLY INVASIVE CARDIAC PROCEDURES

(75) Inventors: Yulun Wang, Goleta, CA (US); Darrin R. Uecker, Santa Barbara, CA (US); Keith Phillip Laby, Santa Barbara, CA (US); Jeff Wilson, Santa Barbara, CA (US); Steve Jordan, Santa Barbara, CA (US); James Wright, Santa Barbara, CA (US)

(73) Assignee: Intuitive Surgical, Inc., Sunnyvale, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/317,890

(22) Filed: Dec. 11, 2002

(65) Prior Publication Data

US 2003/0139733 A1 Jul. 24, 2003

Related U.S. Application Data

(63) Continuation of application No. 09/000,934, filed on Dec. 30, 1997, now Pat. No. 6,905,491, which is a continuation of application No. 08/603,543, filed on Feb. 20, 1996, now Pat. No. 5,762,458.

(51) Int. Cl.
*A61B 1/00* (2006.01)
*A61B 1/04* (2006.01)

(52) U.S. Cl. .................. 600/102; 600/109; 606/130; 901/2; 901/16

(58) Field of Classification Search ............... 606/1, 606/10, 11, 13, 41, 43, 106, 107, 196, 130; 600/101–104, 106–109, 114; 704/3, 200–210, 704/231; 414/2; 901/2, 6, 8–10, 14–18, 901/30, 36, 46
See application file for complete search history.

(56) References Cited

U.S. PATENT DOCUMENTS 977,825 A 12/1910 Murphy (Continued)

FOREIGN PATENT DOCUMENTS

DE 004101242 A1 * 1/1991

(Continued)

OTHER PUBLICATIONS

Abstract of a presentation "3 D Vision Technology Applied to Advanced Minimally Invasive Surgery Systems" (Session 15/3) given at the 3rd World Congress of Endoscopic Surgery in Bordeaux, Jun. 18-20, 1992, (1 page total).

(Continued)

*Primary Examiner*—Ahmed M Farah

(57) ABSTRACT

A system for performing minimally invasive cardiac procedures includes a pair of surgical instruments that are coupled to a pair of robotic arms. The instruments have end effectors that can be manipulated to hold and suture tissue. The robotic arms are coupled to a pair of master handles by a controller. The handles can be moved by the surgeon to produce a corresponding movement of the end effectors. The system may also have a robotically controlled endoscope which allows the surgeon to remotely view the surgical site.

18 Claims, 7 Drawing Sheets

U.S. PATENT DOCUMENTS

| | | | |
|---|---|---|---|
| 3,171,549 A | 3/1965 | Orloff | |
| 3,280,991 A | 10/1966 | Melton et al. | |
| 3,710,798 A * | 1/1973 | Bredemeier | 606/11 |
| 4,058,001 A | 11/1977 | Waxman | |
| 4,128,880 A | 12/1978 | Cray, Jr. | |
| 4,221,997 A | 9/1980 | Flemming | |
| 4,367,998 A | 1/1983 | Causer | |
| 4,401,852 A | 8/1983 | Noso et al. | |
| 4,456,961 A | 6/1984 | Price et al. | |
| 4,460,302 A | 7/1984 | Moreau et al. | |
| 4,474,174 A | 10/1984 | Petruzzi | |
| 4,491,135 A | 1/1985 | Klein | |
| 4,503,854 A * | 3/1985 | Jako | 606/11 |
| 4,517,963 A | 5/1985 | Michel | |
| 4,523,884 A | 6/1985 | Clement et al. | |
| 4,586,398 A | 5/1986 | Yindra | |
| 4,604,016 A | 8/1986 | Joyce | |
| 4,616,637 A | 10/1986 | Caspari et al. | |
| 4,624,011 A | 11/1986 | Watanabe et al. | |
| 4,633,389 A | 12/1986 | Tanaka et al. | |
| 4,635,292 A | 1/1987 | Mori et al. | |
| 4,641,292 A | 2/1987 | Tunnell et al. | |
| 4,655,257 A | 4/1987 | Iwashita | |
| 4,672,963 A | 6/1987 | Barken | |
| 4,676,243 A | 6/1987 | Clayman | |
| 4,728,974 A | 3/1988 | Nio et al. | |
| 4,762,455 A | 8/1988 | Coughlan et al. | |
| 4,791,934 A | 12/1988 | Brunnett | |
| 4,791,940 A | 12/1988 | Hirschfeld et al. | |
| 4,794,912 A | 1/1989 | Lia | |
| 4,815,006 A | 3/1989 | Andersson et al. | |
| 4,815,450 A | 3/1989 | Patel | |
| 4,837,734 A | 6/1989 | Ichikawa et al. | |
| 4,837,754 A | 6/1989 | Nakagawa | |
| 4,852,083 A | 7/1989 | Niehaus et al. | |
| 4,853,874 A | 8/1989 | Iwamoto et al. | |
| 4,854,301 A | 8/1989 | Nakajima | |
| 4,860,215 A | 8/1989 | Seraji | |
| 4,863,133 A | 9/1989 | Bonnell | |
| 4,883,400 A | 11/1989 | Kuban et al. | |
| 4,896,673 A * | 1/1990 | Rose et al. | 600/439 |
| 4,930,494 A | 6/1990 | Takehana et al. | |
| 4,945,479 A | 7/1990 | Rusterholz et al. | |
| 4,949,717 A | 8/1990 | Shaw | |
| 4,954,952 A | 9/1990 | Ubhayakar et al. | |
| 4,965,417 A | 10/1990 | Massie | |
| 4,969,709 A | 11/1990 | Sogawa et al. | |
| 4,969,890 A | 11/1990 | Sugita et al. | |
| 4,979,949 A | 12/1990 | Matsen, III et al. | |
| 4,980,626 A | 12/1990 | Hess et al. | |
| 4,989,253 A | 1/1991 | Liang et al. | |
| 4,996,975 A | 3/1991 | Nakamura | |
| 5,019,968 A | 5/1991 | Wang et al. | |
| 5,020,001 A | 5/1991 | Yamamoto et al. | |
| 5,024,652 A * | 6/1991 | Dumenek et al. | 604/22 |
| 5,065,741 A | 11/1991 | Uchiyama et al. | |
| 5,078,140 A | 1/1992 | Kwoh | |
| 5,086,401 A | 2/1992 | Glassman et al. | |
| 5,091,656 A | 2/1992 | Gahn | |
| 5,097,829 A | 3/1992 | Quisenberry | |
| 5,097,839 A | 3/1992 | Allen | |
| 5,098,426 A | 3/1992 | Sklar et al. | |
| 5,100,138 A * | 3/1992 | Wilde | 273/440.1 |
| 5,105,367 A | 4/1992 | Tsuchihashi et al. | |
| 5,109,499 A | 4/1992 | Inagami et al. | |
| 5,123,095 A | 6/1992 | Papadopoulos et al. | |
| 5,131,105 A | 7/1992 | Harrawood et al. | |
| 5,142,930 A | 9/1992 | Allen et al. | |
| 5,145,227 A | 9/1992 | Monford, Jr. | |
| 5,166,513 A | 11/1992 | Keenan et al. | |
| 5,175,694 A | 12/1992 | Amato | |
| 5,182,641 A * | 1/1993 | Diner et al. | 348/86 |
| 5,184,601 A | 2/1993 | Putman | |
| 5,187,574 A | 2/1993 | Kosemura et al. | |
| 5,196,688 A | 3/1993 | Hesse et al. | |
| 5,201,325 A | 4/1993 | McEwen et al. | |
| 5,201,743 A | 4/1993 | Haber et al. | |
| 5,217,003 A | 6/1993 | Wilk | |
| 5,221,283 A | 6/1993 | Chang | |
| 5,228,429 A | 7/1993 | Hatano | |
| 5,230,623 A | 7/1993 | Guthrie et al. | |
| 5,236,432 A * | 8/1993 | Matsen et al. | 606/88 |
| 5,251,127 A | 10/1993 | Raab | |
| 5,271,384 A | 12/1993 | McEwen et al. | |
| 5,279,309 A | 1/1994 | Taylor et al. | |
| 5,282,806 A | 2/1994 | Haber et al. | |
| 5,289,273 A | 2/1994 | Lang | |
| 5,289,365 A | 2/1994 | Caldwell et al. | |
| 5,299,288 A | 3/1994 | Glassman et al. | |
| 5,300,926 A | 4/1994 | Stoeckl | |
| 5,303,148 A | 4/1994 | Mattson et al. | |
| 5,304,185 A | 4/1994 | Taylor | |
| 5,305,203 A | 4/1994 | Raab | |
| 5,305,427 A | 4/1994 | Nagata | |
| 5,309,717 A | 5/1994 | Minch | |
| 5,313,306 A | 5/1994 | Kuban et al. | |
| 5,320,630 A | 6/1994 | Ahmed | |
| 5,337,732 A | 8/1994 | Grundfest et al. | |
| 5,339,799 A | 8/1994 | Kami et al. | |
| 5,343,385 A | 8/1994 | Joskowicz et al. | |
| 5,343,391 A | 8/1994 | Mushabac | |
| 5,345,538 A | 9/1994 | Narayannan et al. | |
| 5,357,962 A | 10/1994 | Green | |
| 5,368,015 A | 11/1994 | Wilk | |
| 5,368,428 A | 11/1994 | Hussey et al. | |
| 5,371,536 A | 12/1994 | Yamaguchi | |
| 5,382,885 A | 1/1995 | Salcudean et al. | |
| 5,388,987 A | 2/1995 | Badoz et al. | |
| 5,395,369 A | 3/1995 | McBrayer et al. | |
| 5,397,323 A | 3/1995 | Taylor et al. | |
| 5,402,801 A | 4/1995 | Taylor | |
| 5,403,319 A | 4/1995 | Matsen, III et al. | |
| 5,408,409 A | 4/1995 | Glassman et al. | |
| 5,410,638 A | 4/1995 | Colgate et al. | |
| 5,417,210 A | 5/1995 | Funda et al. | |
| 5,417,701 A | 5/1995 | Holmes | |
| 5,422,521 A | 6/1995 | Neer et al. | |
| 5,431,645 A | 7/1995 | Smith et al. | |
| 5,434,457 A | 7/1995 | Josephs et al. | |
| 5,442,728 A | 8/1995 | Kaufman et al. | |
| 5,445,166 A | 8/1995 | Taylor | |
| 5,451,924 A | 9/1995 | Massimino et al. | |
| 5,455,766 A | 10/1995 | Scheller et al. | |
| 5,458,547 A | 10/1995 | Teraoka et al. | |
| 5,458,574 A | 10/1995 | Machold et al. | |
| 5,476,010 A | 12/1995 | Fleming et al. | |
| 5,490,117 A | 2/1996 | Oda et al. | |
| 5,506,912 A | 4/1996 | Nagasaki et al. | |
| 5,512,919 A | 4/1996 | Araki | |
| 5,515,478 A * | 5/1996 | Wang | 700/251 |
| 5,544,654 A | 8/1996 | Murphy et al. | |
| 5,553,198 A | 9/1996 | Wang et al. | |
| 5,562,503 A | 10/1996 | Ellman et al. | |
| 5,571,110 A | 11/1996 | Matsen, III et al. | |
| 5,572,999 A | 11/1996 | Funda et al. | |
| 5,609,560 A | 3/1997 | Ichikawa et al. | |
| 5,626,595 A | 5/1997 | Sklar et al. | |
| 5,629,594 A | 5/1997 | Jacobus et al. | |
| 5,630,431 A | 5/1997 | Taylor | |
| 5,631,973 A | 5/1997 | Green | |
| 5,636,259 A | 6/1997 | Khutoryansky et al. | |
| 5,649,956 A | 7/1997 | Jensen et al. | |
| 5,657,429 A | 8/1997 | Wang et al. | |
| 5,658,250 A | 8/1997 | Blomquist et al. | |

| | | | |
|---|---|---|---|
| 5,676,673 A | 10/1997 | Ferre et al. | |
| 5,695,500 A | 12/1997 | Taylor et al. | |
| 5,696,574 A | 12/1997 | Schwaegerle | |
| 5,696,837 A | 12/1997 | Green | |
| 5,697,285 A * | 12/1997 | Nappi et al. | 91/519 |
| 5,718,038 A | 2/1998 | Takiar et al. | |
| 5,735,290 A | 4/1998 | Sterman et al. | |
| 5,737,711 A | 4/1998 | Abe | |
| 5,749,362 A | 5/1998 | Funda et al. | |
| 5,754,741 A * | 5/1998 | Wang et al. | 700/251 |
| 5,762,458 A * | 6/1998 | Wang et al. | 414/1 |
| 5,776,126 A | 7/1998 | Wilk et al. | |
| 5,779,623 A | 7/1998 | Bonnell | |
| 5,800,423 A | 9/1998 | Jensen | |
| 5,807,284 A | 9/1998 | Foxlin | |
| 5,807,378 A | 9/1998 | Jensen et al. | |
| 5,808,665 A * | 9/1998 | Green | 348/65 |
| 5,810,880 A | 9/1998 | Jensen et al. | |
| 5,813,813 A | 9/1998 | Daum et al. | |
| 5,814,038 A | 9/1998 | Jensen et al. | |
| 5,817,084 A | 10/1998 | Jensen | |
| 5,825,982 A | 10/1998 | Wright et al. | |
| 5,836,869 A | 11/1998 | Kudo et al. | |
| 5,844,824 A | 12/1998 | Newman et al. | |
| 5,859,934 A | 1/1999 | Green | |
| 5,860,995 A | 1/1999 | Berkelaar | |
| 5,876,325 A | 3/1999 | Mizuno et al. | |
| 5,878,193 A | 3/1999 | Wang et al. | |
| 5,882,206 A | 3/1999 | Gillio | |
| 5,887,121 A | 3/1999 | Funda et al. | |
| 5,931,832 A | 8/1999 | Jensen | |
| 5,950,629 A | 9/1999 | Taylor et al. | |
| 6,009,346 A * | 12/1999 | Ostrow | 604/20 |
| 6,024,695 A | 2/2000 | Taylor et al. | |
| 6,102,850 A * | 8/2000 | Wang et al. | 600/102 |
| 6,120,433 A | 9/2000 | Mizuno et al. | |
| 6,201,984 B1 * | 3/2001 | Funda et al. | 600/407 |
| 6,223,100 B1 * | 4/2001 | Green | 700/264 |
| 6,278,975 B1 | 8/2001 | Brant et al. | |
| 6,368,269 B1 * | 4/2002 | Lane | 600/126 |
| 6,714,841 B1 * | 3/2004 | Wright et al. | 700/259 |
| 6,817,972 B2 * | 11/2004 | Snow | 600/37 |

FOREIGN PATENT DOCUMENTS

| | | |
|---|---|---|
| DE | 9204118 | 7/1992 |
| EP | 239409 | 9/1987 |
| EP | 424687 | 5/1991 |
| EP | 776738 | 6/1997 |
| WO | WO-9104711 | 4/1991 |
| WO | WO-9220295 | 11/1992 |
| WO | WO-9313916 | 7/1993 |
| WO | WO-9418881 | 9/1994 |
| WO | WO-9426167 | 11/1994 |
| WO | WO-9715240 | 5/1997 |
| WO | WO-9825666 | 6/1998 |

OTHER PUBLICATIONS

Abstract of a presentation "A Pneumatic Controlled Sewing Device for Endoscopic Application the MIS Sewing Instrument MSI" given at the 3rd World Congress of Endoscopic Surgery in Bordeaux, Jun. 18, 20, 1992, (1 page total).

Abstract of a presentation given at the 3rd World Congress of Endoscopic Surgery in Bordeaux entitled "Session 15/1", Jun. 18-20, 1992.

Abstract of a presentation given at the 3rd World Congress of Endoscopic Surgery in Bordeaux entitled "Session 15/4", Jun. 18 to 20, 1992, (1 page total).

Abstract of a presentation given at the 3rd World Congress of Endoscopic Surgery in Bordeaux entitled "Session 15/5", Jun. 18 to 20, 1992, (1 page total).

Abstract of a presentation given at the 3rd World Congress of Endoscopic Surgery in Bordeaux, entitled "Session 15/2", Jun. 18-20, 1992, 1 page total.

Bejczy, A.K. et al., "Controlling Remote Manipulators through Kinesthetic Coupling", Computers in Mechanical Engineering, 1983, pp. 48-60, vol. 1-Issue 1.

Ben Gayed et al. An Advanced Control Micromanipulator for Surgical Applications, Systems Science, 1987, pp. 123-134, vol. 13.

Besant et al., Camera Control for Laparoscopic Surgery by Speech recognizing Robot: Constant Attention and Better Use of Personnel, 3rd World Congress of Endoscopic surgery, 1993, p. 271, vol. 3-issue 3.

Charles, S. et al., Design of a Surgeon Machine Interface for Teleoperated Microsurgery, Proceedings of Annual Conference on Engineering in Medicine and Biology, 1989, pp. 0883-0884, vol. 11, IEEE.

Colgate, J.E., Power and Impedance Scaling in Bilateral Manipulation, IEEE International Conference on Robotics and Automation, Sacramento, California, Apr. 1991, pp. 2292-2297, vol. 3, IEEE.

Corcoran, Elizabeth, Robots for the Operating Room, The New York Times, 2 pages total, Jul. 19, 1992, Section 3 p. 9C.

Das, Hari et al., Kinematic Control and Visual Display of Redundant Teleoperators, IEEE International Conference on Systems, Man, and Cybernetics, 1989, pp. 1072-1077, vol. 3, IEEE.

Dolan J.M. et al., A Robot in an Operating Room: A Bull in a China Shop, 1987, pp. 1096-1097, vol. 2.

Brief Communication, mailed Jun. 2002, for EP Patent No. EP 0653922 B, including Affidavit by Alberic George T.W. Fiennes signed May 20, 2002 relating to Besant Abstract and NASA presentation by Keith L. Doty, "Kinematic Analysis of the Arid Manipulator" given on Aug. 7, 1992 at the Univ. of Florida, Gainesville, FL (52 pp.).

Green, Philip S. et al., Abstract No. 704 of a presentation "Telepresence: Advanced Teleoperator Technology for Minimally Invasive Surgery," given at the 3rd World Congress of Endoscopic Surgery in Bordeaux, Jun. 18, 20, 1992 -"Session CL25/5" (2 pages total). .

Guerrouad, Aicha et al., S.M.O.S.: Stereotaxical Microtelemanipulator for Ocular Surgery, IEEE Engineering in Medicine and Biology Society 11th Annual Int'l Conf, 1989, pp. 879-880, IEEE.

Inoue, Six-Axis bileteral control of an articulated slave manipulator using a Cartesian master manipulator, Advanced robotics, 1990, pp. 139-150, vol. 4-Issue 2, Robotic society of Japan.

Jau, B. M., Anthropomorphic Remote Manipulator, NASA Tech Briefs, Apr. 1991, pp. 92, NASA's Jet Propulsion Laboratory, Pasadena, California.

Kazerooni, H, Human/Robot Interaction via the Transfer of Power and Information Signals--Part II, An Experimental Analysis, Proc. fo the 1989 IEEE International Conference on Robotics and Automation, 1989, pp. 1641-1647, vol. 3, IEEE.

Kazerooni, H., Human/Robot Interaction via the Transfer of Power and Information Signals Part I: Dynamics and Control Analysis, 1989, pp. 1632-1640, IEEE.

Krishnan, S.M. et al., Abstract of a presentation "Design Considerations of a New Generation Endoscope Using Robotics and Computer Vision Technology" given at the 3rd World Congress of Endoscopic Surgery in Bordeaux, Jun. 18-20, 1992, (1 page total). .

Lavallee, A New System for Computer Assisted Neurosurgery, Journal: Eng. in Med. and Biol. Soc, Jun. 1989, pp. 926-927, vol. 11.

Mair, Gordon M., "Industrial Robotics," Prentice Hall, 1988, pp. 41-43, 49-50, 54, 203-209.

Majima et al., On a Micro Manipulator for Medical Application Stability Consideration of its Bilateral Controller Mechatronics, 1991, pp. 293-309, vol. 1- Issue 3.

Notice of Opposition European Patent Office dated, Sep. 14, 2000, pp. 1-27.

Preising, B. et al., A Literature Review: Robots in Medicine, IEEE Engineering in Medicine and Biology, 1991, pp. 13-22, 71, vol. 10 - Issue 2, IEEE.

Sabatini, A. M. et al., Force Feedback Based Telemicromanipulation for Robot Surgery on Soft Tissue, IEEE Engineering in Medicine and Biology Society 11th Annual International Conference, 1989, pp. 890-891, vol. 3, IEEE.

Summons to Attend Oral Proceedings Pursuant to Rule EPC mailed 13 for Patent No. EP 0653922 B, Mar. 2002, (28 pgs total), vol. 71 - Issue 1.

Taubes et al., "Surgery in cyberspace", Discover magazine, Dec. 1994, vol. 15 - Issue 12, pp. 85-92.

Taylor, Russell H. et al., Taming the Bull: Safety in a Precise Surgical Robot, 1991, pp. 865-870, IEEE.

Tejima et al., "A New Microsurgical Robot System for Corneal Transplantation," Precision Machinery, 1988, pp. 1-9, vol. 2, Gordon and Breach Science Publishers Inc.

Tendick, Frank et al., "Analysis of the Surgeon's Grasp for Telerobotic Surgical Manipulation," IEEE Engineering in Medicine and Biology 11th Annual Int Conf, Jun. 1989, pp. 914-915, IEEE.

Thring, M.W., "Robots and telechirs: manipulators with memory remote manipulators machine limbs for the handicapped," 1983, pp. 9-279.

Transcript of a video presented by SRI at the 3rd World Congress of Endoscopic Surgery in Bordeaux on Jun. in Washington on and in San Diego CA on entitled, Telepresence Surgery The Future of Minimally Invasive Medicine, Apr. 9, 1992 ,Jun. 18, (3 pages total).

Trevelyan, James P. et al., Motion Control for a Sheep Shearign Robot, IEEE Robotics Research Conference, the 1st International Symposium, Carroll, NH, USA., 1983, pp. 175-190, MIT Press.

Vibet, C., Properties of Master Slave Robots, Motor con, 1987, pp. 309-316.

Video presented by SRI at the 3rd World Congress of Endoscopic Surgery in Bordeaux on in Washington on Apr. 9, 1992 and in San Diego CA on entitled Telepresence Surgery The Future of Minimally Invasive Medicine (VHS Tape), Jun. 4-7, 1992.

Wolf et al., Student Reference Manual for Elecrtonic Instrumentation Laboratories, 1990, pp. 498 and 499, Prentice Hall New Jersey.

Green et al., Abstract of a presentation "Telepresence: Advanced Teleoperator Technology for Minimally Invasive Surgery" given at Medicine Meets Virtual Reality: Discovering Applications for 3-D Multi-Media Interactive Technology in the Health Sciences; Jun. 4-7, 1992.

Green et al., Statutory Declaration presenter of the video entitled Telepresence Surgery The Future of Minmally Invasive Medicine, (32 page total), Dr Philip S Green; Sep. 12, 2000.

Minutes of the Oral Proceedings Before the Opposition Division, for EP Application No. 93 919 884.2 (Patent No. EP 0653922 B) between Computer Motion, Inc. v. Intuitive Surgical, Inc.; Jul. 24, 2002.

* cited by examiner

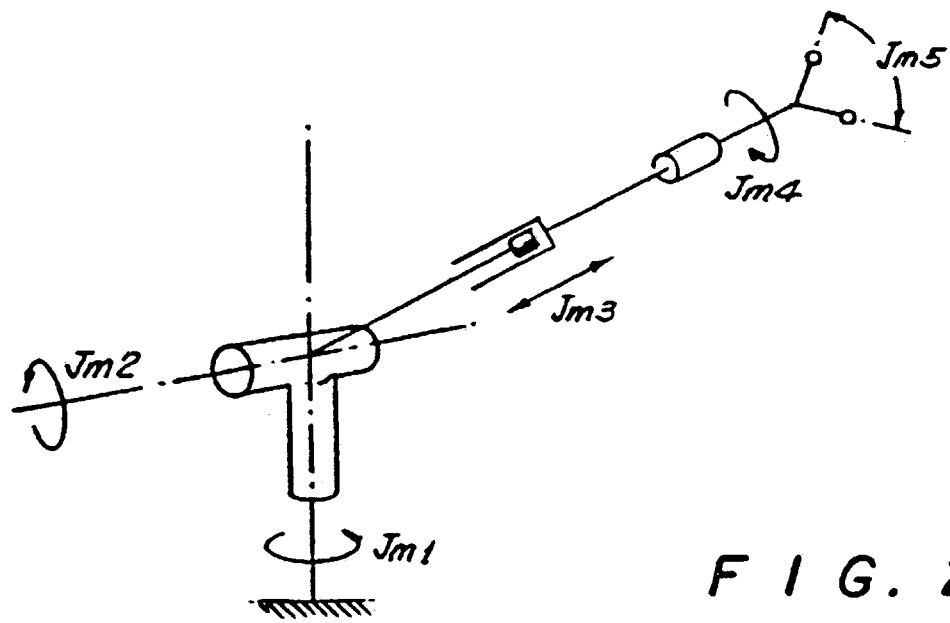
F I G. 2
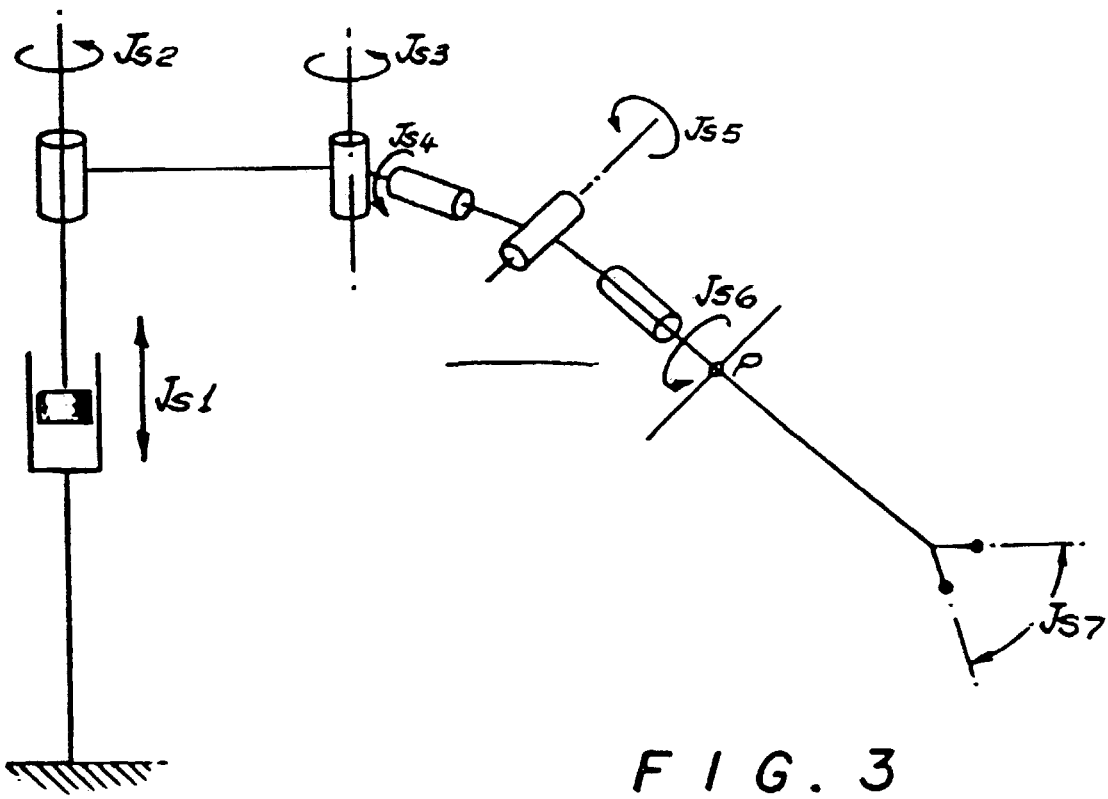
F I G. 3

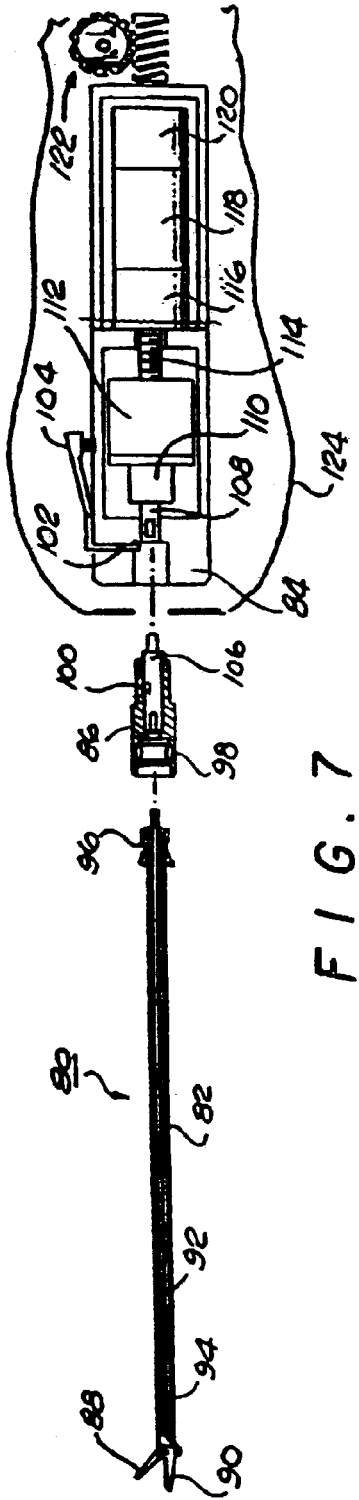
FIG. 7
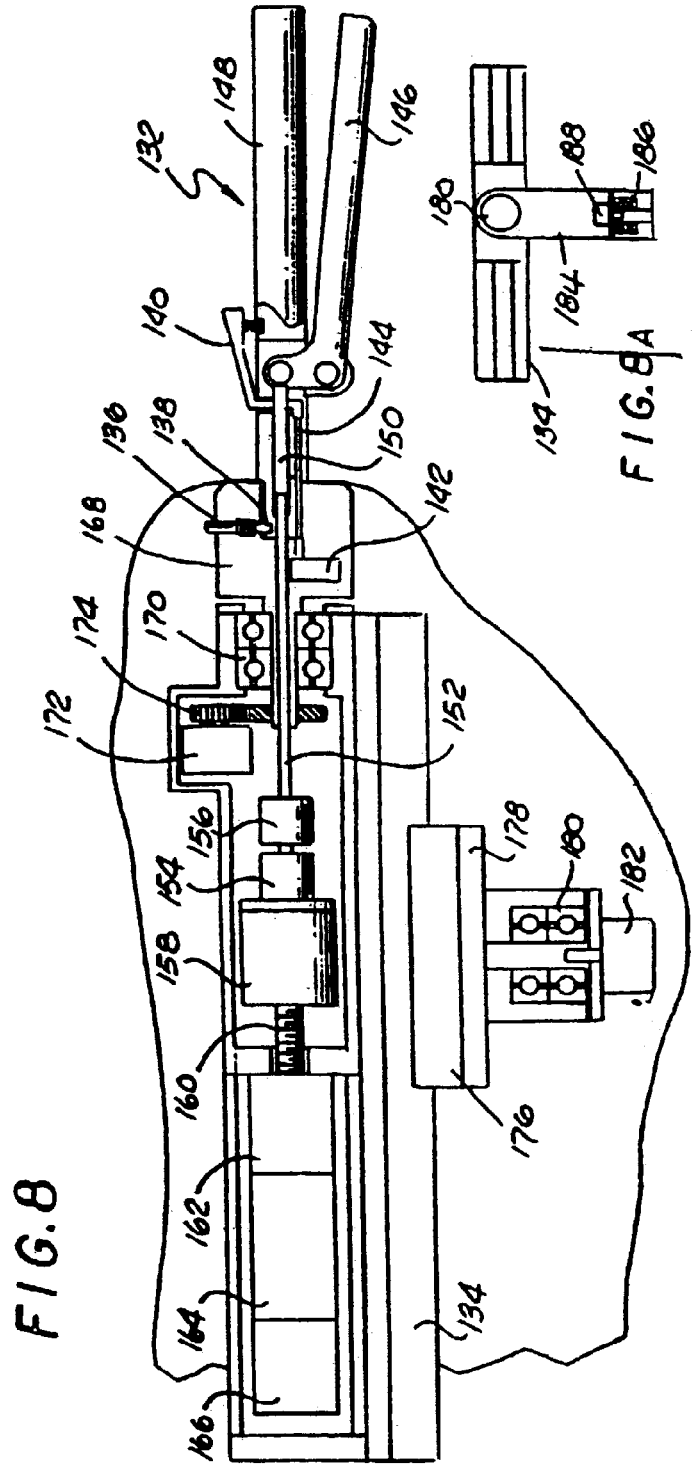
FIG. 8
FIG. 8A

METHOD AND APPARATUS FOR PERFORMING MINIMALLY INVASIVE CARDIAC PROCEDURES

REFERENCE TO CROSS-RELATED APPLICATIONS

This is a continuation of application Ser. No. 09/000,934, filed on Dec. 30, 1997 now U.S. Pat. No. 6,905,491, which is a continuation of application Ser. No. 08/603,543, filed on Feb. 20, 1996, U.S. Pat. No. 5,762,458.

BACKGROUND OF THE INVENTION

1. Field of the Invention

The present invention relates to a system and method for performing minimally invasive cardiac procedures.

2. Description of Related Art

Blockage of a coronary artery may deprive the heart of the blood and oxygen required to sustain life. The blockage may be removed with medication or by an angioplasty. For severe blockage a coronary artery bypass graft (CABG) is performed to bypass the blocked area of the artery. CABG procedures are typically performed by splitting the sternum and pulling open the chest cavity to provide access to the heart. An incision is made in the artery adjacent to the blocked area. The internal mammary artery (IMA) is then severed and attached to the artery at the point of incision. The IMA bypasses the blocked area of the artery to again provide a full flow of blood to the heart. Splitting the sternum and opening the chest cavity can create a tremendous trauma on the patient. Additionally, the cracked sternum prolongs the recovery period of the patient.

There have been attempts to perform CABG procedures without opening the chest cavity. Minimally invasive procedures are conducted by inserting surgical instruments and an endoscope through small incision in the skin of the patient. Manipulating such instruments can be awkward, particularly when suturing a graft to a artery. It has been found that a high level of dexterity is required to accurately control the instruments. Additionally, human hands typically have at least a minimal amount of tremor. The tremor further increases the difficulty of performing minimal invasive cardiac procedures. It would be desirable to provide a system for effectively performing minimally invasive coronary artery bypass graft procedures.

SUMMARY OF THE INVENTION

The present invention is a system for performing minimally invasive cardiac procedures. The system includes a pair of surgical instruments that are coupled to a pair of robotic arms. The instruments have end effectors that can be manipulated to hold and suture tissue. The robotic arms are coupled to a pair of master handles by a controller. The handles can be moved by the surgeon to produce a corresponding movement of the end effectors. The movement of the handles is scaled so that the end effectors have a corresponding movement that is different, typically smaller, than the movement performed by the hands of the surgeon. The scale factor is adjustable so that the surgeon can control the resolution of the end effector movement. The movement of the end effector can be controlled by an input button, so that the end effector only moves when the button is depressed by the surgeon. The input button allows the surgeon to adjust the position of the handles without moving the end effector, so that the handles can be moved to a more comfortable position. The system may also have a robotically controlled endoscope which allows the surgeon to remotely view the surgical site. A cardiac procedure can be performed by making small incisions in the patient's skin and inserting the instruments and endoscope into the patient. The surgeon manipulates the handles and moves the end effectors to perform a cardiac procedure such as a coronary artery bypass graft.

BRIEF DESCRIPTION OF THE DRAWINGS

The objects and advantages of the present invention will become more readily apparent to those ordinarily skilled in the art after reviewing the following detailed description and accompanying drawings, wherein:

FIG. 2 is a schematic of a master of the system;

FIG. 3 is a schematic of a slave of the system;

FIG. 7 is an exploded view of an end effector of the system;

FIG. 8 is a top view of a master handle of the system;

FIG. 8a is a side view of the master handle;

DETAILED DESCRIPTION OF THE INVENTION

Figure 1:
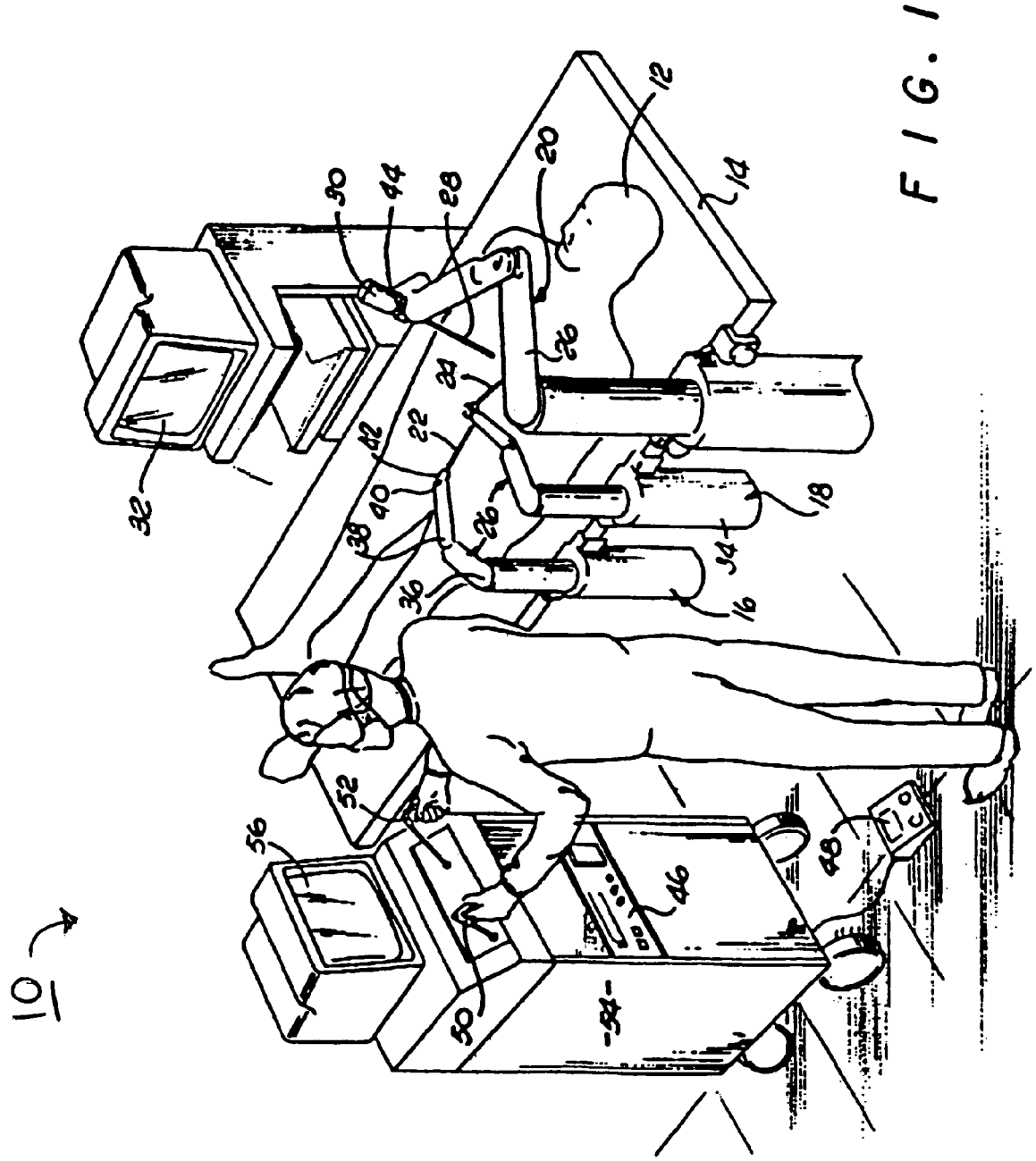
FIG. 1 is a perspective view of a minimally invasive surgical system of the present invention.

Referring to the drawings more particularly by reference numbers, FIG. 1 shows a system 10 that can perform minimally invasive surgery. In the preferred embodiment, the system 10 is used to perform a minimally invasive coronary artery bypass graft (MI-CABG) and other anastomostic procedures. Although a MI-CABG procedure is shown and described, it is to be understood that the system may be used for other surgical procedures. For example, the system can be used to suture any pair of vessels.

The system 10 is used to perform a procedure on a patient 12 that is typically lying on an operating table 14. Mounted to the operating table 14 is a first articulate arm 16, a second articulate arm 18 and a third articulate arm 20. The articulate arms 16, 18, 20 are preferably mounted to the table so that the arms are at a same reference plane as the patient. Although three articulate arms are shown and described, it is to be understood that the system may have any number of arms.

The first and second articulate arms 16 and 18 each have a surgical instrument 22 and 24 coupled to a robotic arm 26. The third articulate arm 20 has an endoscope 28 that is held by a robotic arm 26. The instruments 22 and 24, and endoscope 28 are inserted through incisions cut into the skin of the patient. The endoscope has a camera 30 that is coupled to a television monitor 32 which displays images of the internal organs of the patient.

The robotic arms 26 each have a linear motor 34, a first rotary motor 36 and a second rotary motor 38. The robotic arms 26 also have a pair of passive joints 40 and 42. The articulate arm 20 also have a worm gear 44 and means to couple the instruments 22 and 24, and endoscope 28 to the robotic arm 26. The first, second, and third articulate arms are coupled to a controller 46 which can control the movement of the arms.

The controller 46 is connected to an input device 48 such as a foot pedal that can be operated by a surgeon to move the location of the endoscope and view a different portion of the patient by depressing a corresponding button(s) of the foot pedal 48. The controller 46 receives the input signals from the foot pedal 48 and moves the robotic arm 26 and endoscope 28 in accordance with the input commands of the surgeon. The robotic arms may be devices that are sold by the assignee of the present invention, Computer Motion, Inc. of Goleta, Calif., under the trademark AESOP. The system is also described in allowed U.S. application Ser. No. 08/305,415, which is hereby incorporated by reference. Although a foot pedal 48 is shown and described, it is to be understood that the system may have other input means such as a hand controller, or a speech recognition interface.

The instruments 22 of the first 16 and second 18 articulate arms are controlled by a pair of master handles 50 and 52 that can be manipulated by the surgeon. The handles 50 and 52, and arms 16 and 18, have a master-slave relationship so that movement of the handles produces a corresponding movement of the surgical instruments. The handles 50 and 52 may be mounted to a portable cabinet 54. A second television monitor 56 may be placed onto the cabinet 54 and coupled to the endoscope 28 so that the surgeon can readily view the internal organs of the patient. The handles 50 and 52 are also coupled to the controller 46. The controller 46 receives input signals from the handles 50 and 52, computes a corresponding movement of the surgical instruments, and provides output signals to move the robotic arms and instruments.

Each handle has multiple degrees of freedom provided by the various joints Jm1-Jm5 depicted in FIG. 2. Joints Jm1 and Jm2 allow the handle to rotate about a pivot point of the cabinet 54. Joint Jm3 allows the surgeon to move the handle into and out of the cabinet 54 in a linear manner. Joint Jm4 allows the surgeon to rotate the master handle about a longitudinal axis of the handle. The joint Jm5 allows a surgeon to open and close a gripper. Each joint Jm1-Jm5 has a position sensor which provides feedback signals that correspond to the relative position of the handle. The position sensors may be potentiometers, or any other feedback device, that provides an electrical signal which corresponds to a change of position.

FIG. 3 shows the various degrees of freedom of each articulate arm 16 and 18. The joints Js1, Js2 and Js3 correspond to the linear motor and rotary motors of the robotic arms 26, respectively. The joints Js4 ard Js5 correspond to the passive joints 40 and 42 of the arms 26. The joint Js6 may be a motor which rotates the surgical instruments about the longitudinal axis of the instrument. The joint Js7 may be a pair of fingers that can open and close. The instruments 22 and 24 move about a pivot point P located at the incision of the patient.

Figure 4:
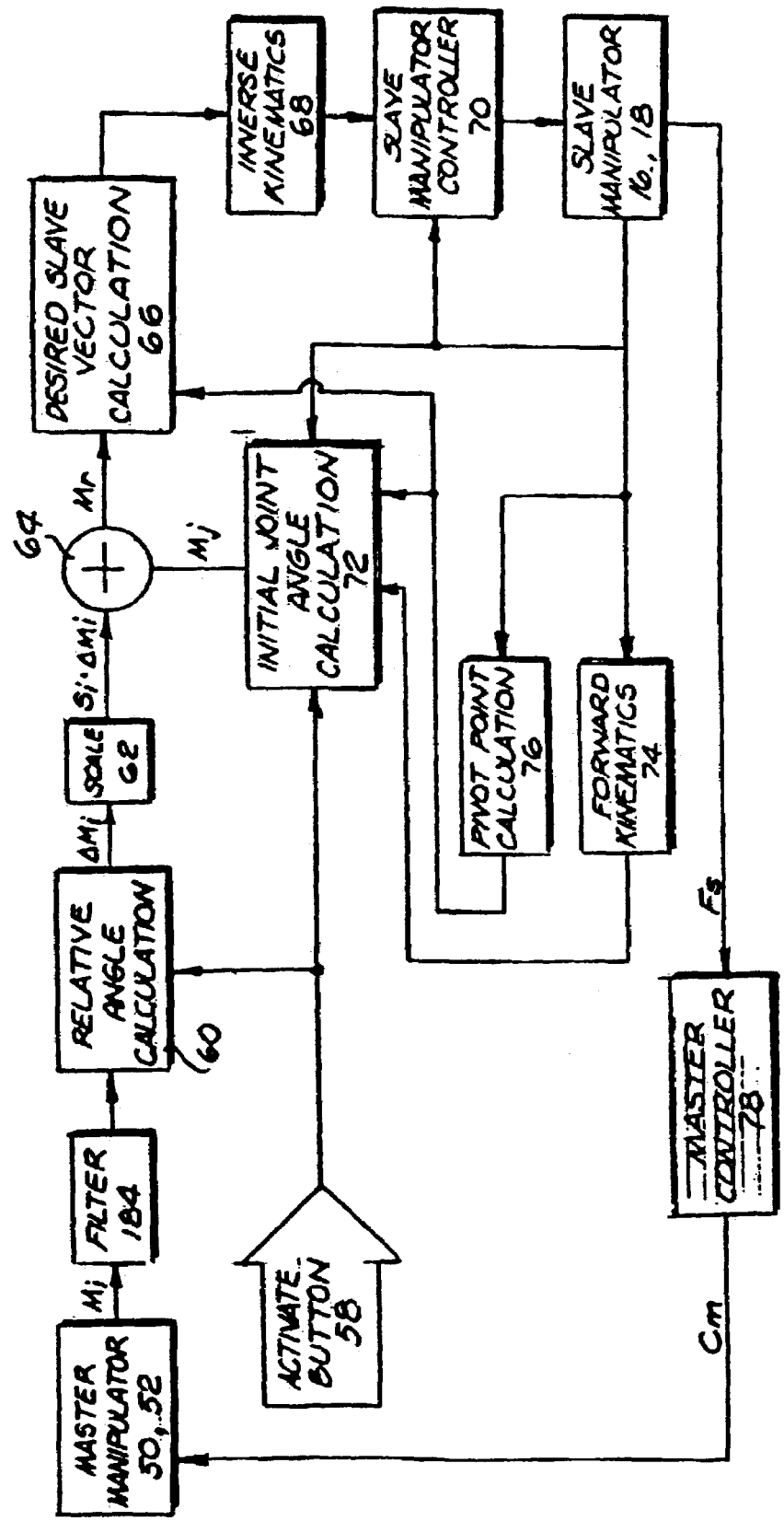
FIG. 4 is a schematic of a control system of the system.

FIG. 4 shows a schematic of a control system that translates a movement of a master handle into a corresponding movement of a surgical instrument. In accordance with the control system shown in FIG. 4, the controller 46 computes output signals for the articulate arms so that the surgical instrument moves in conjunction with the movement of the handle. Each handle may have an input button 58 which enables the instrument to move with the handle. When the input button 58 is depressed the surgical instrument follows the movement of the handle. When the button 58 is released the instrument does not track the movement of the handle. In this manner the surgeon can adjust or "ratchet" the position of the handle without creating a corresponding undesirable movement of the instrument. The "ratchet" feature allows the surgeon to continuously move the handles to more desirable positions without altering the positions of the arms. Additionally, because the handles are constrained by a pivot point the ratchet feature allows the surgeon to move the instruments beyond the dimensional limitations of the handles. Although an input button is shown and described, it is to be understood that the surgical instrument may be activated by other means such as voice recognition. The input button may be latched so that activation of the instrument toggles between active and inactive each time the button is depressed by the surgeon.

When the surgeon moves a handle, the position sensors provide feedback signals M1-M5 that correspond to the movement of the joints Jm1-JmS, respectively. The controller 46 computes the difference between the new handle position and the original handle position in compution block 60 to generate incremental position values $\Delta M1$-$\Delta M5$.

The incremental position values $\Delta M1$-$\Delta M5$ are multiplied by scale factors S1-S5, respectively in block 62. The scale factors are typically set at less than one so that the movement of the instrument is less than the movement of the handle. In this manner the surgeon can produce very fine movements of the instruments with relatively coarse movements of the handles. The scale factors S1-S5 are variable so that the surgeon can vary the resolution of instrument movement. Each scale factor is preferably individually variable so that the surgeon can more finely control the instrument in certain directions. By way of example, by setting one of the scale factors at zero the surgeon can prevent the instrument from moving in one direction. This may be advantageous if the surgeon does not want the surgical instrument to contact an organ or certain tissue located in a certain direction relative to the patient. Although scale factors smaller than a unit one described, it is to be understood that a scale factor may be greater than one. For example, it may be desirable to spin the instrument at a greater rate than a corresponding spin of the handle.

The controller 46 adds the incremental values $\Delta M1$-$\Delta M5$ to the initial joint angles Mj1-Mj5 in adder element 64 to provide values Mr1-Mr5. The controller 46 then computes desired slave vector calculations in computation block 66 in accordance with the following equations.

$Rdx = Mr3 \cdot \sin(Mr1) \cdot \cos(Mr2) + Px$ $Rdy = Mr3 \cdot \sin(Mr1) \cdot \sin(Mr2) + Py$ $Rdz = Mr3 \cdot \cos(Mr1) + Pz$ $Sdr = Mr4$ $Sdg = Mr5$ where;

Rdx,y,z=the new desired position of the end effector of the instrument.

Sdr=the angular rotation of the instrument about the instrument longitudinal axis.

Sdg=the amount of movement of the instrument fingers.

Px,y,z=the position of the pivot point P.

The controller 46 then computes the movement of the robotic arm 26 in computational block 68 in accordance with the following equations.

$Jsd1 = Rdz$ $$Jsd3 = \pi - \cos^{-1}\left[\frac{Rdx^2 + Rdy^2 - L1^2 - L2^2}{2L1 \cdot L2}\right]$$

$Jsd2 = \tan^{-1}(Rdy/Rdx) + \Delta$ for $Jsd3 \leq 0$ $Jsd2 = \tan^{-1}(Rdy/Rdx) - \Delta$ for $Jsd3 > 0$ $$\Delta = \cos^{-1}\left[\frac{Rdx^2 + Rdy^2 - L1^2 - L2^2}{2 \cdot L1\sqrt{Rdx^2 + Rdy^2}}\right]$$

$Jsd6 = Mr4$ $Jsd7 = Mr5$ where;
 $Jsd1$ = the movement of the linear motor.
 $Jsd2$ = the movement of the first rotary motor.
 $Jsd3$ = the movement of the second rotary motor.
 $Jsd6$ = the movement of the rotational motor.
 $Jsd7$ = the movement of the gripper.
 $L1$ = the length of the linkage arm between the first rotary motor and the second rotary motor.
 $L2$ = the length of the linkage arm between the second rotary motor and the passive joints.

The controller provides output signals to the motors to move the arm and instrument in the desired location in block 70. This process is repeated for each movement of the handle.

The master handle will have a different spatial position relative to the surgical instrument if the surgeon releases the input button and moves the handle. When the input button 58 is initially depressed, the controller 46 computes initial joint angles $Mj1$-$Mj5$ in computational block 72 with the following equations.

$Mj1 = \tan^{-1}(ty/tx)$ $Mj2 = \tan^{-1}(d/tz)$ $Mj3 = D$ $Mj4 = Js6$ $Mj5 = Js7$ $d = \sqrt{tx^2 + ty^2}$ $$tx = \frac{Rsx - Px}{D} \quad ty = \frac{Rsy - Py}{D} \quad tz = \frac{Rsz - Pz}{D}$$

The forward kinematic values are computed in block 74 with the following equations.

Figure 5:
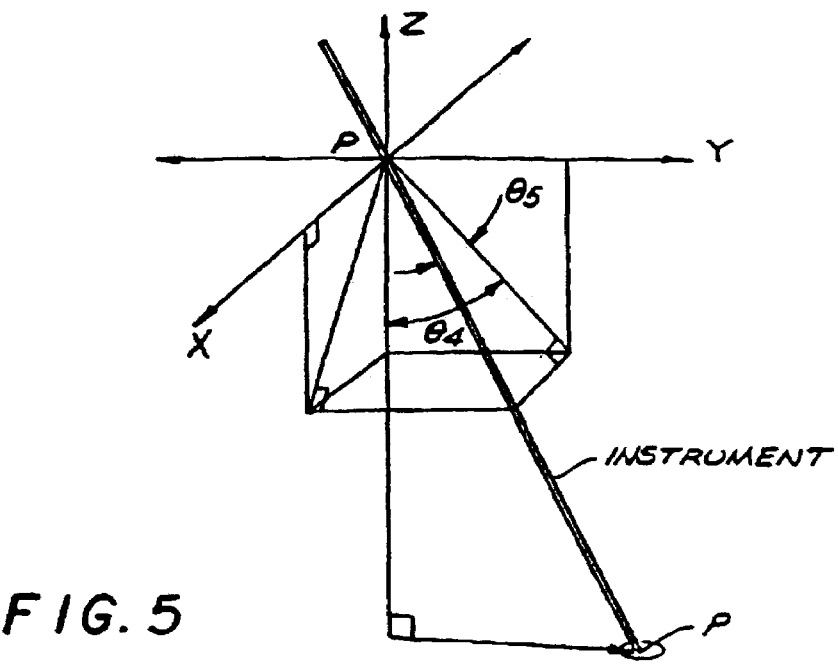
FIG. 5 is a schematic showing the instrument in a coordinate frame.

$Rsx = L1 \cdot \cos(Js2) + L2 \cdot \cos(Js2 + Js3)$ $Rsy = L1 \cdot \cos(Js2) + L2 \cdot \sin(Js2 + Js3)$ $Rsz = J1$ The joint angles $Mj$ are provided to adder 64. The pivot points $Px$, $Py$ and $Pz$ are computed in computational block 76 as follows. The pivot point is calculated by initially determining the original position of the intersection of the end effector and the instrument PO, and the unit vector Uo which has the same orientation as the instrument. The position $P(x, y, z)$ values can be derived from various position sensors of the robotic arm. Referring to FIG. 5 the instrument is within a first coordinate frame (x, y, z) which has the angles $\theta 4$ and $\theta 5$. The unit vector Uo is computed by the transformation matrix:

$$Uo = \begin{bmatrix} \cos\Theta_5 & 0 & -\sin\Theta_5 \\ -\sin\Theta_4\sin\Theta_5 & \cos\Theta_4 & -\sin\Theta_4\cos\Theta_5 \\ \cos\Theta_4\sin\Theta_5 & \sin\Theta_4 & \cos\Theta_4 \end{bmatrix} \begin{bmatrix} 0 \\ 0 \\ -1 \end{bmatrix}$$

After each movement of the end effector an angular movement of the instrument $\Delta\theta$ is computed by taking the arcsin of the cross-product of the first and second unit vectors Uo and U1 of the instrument in accordance with the following line equations Lo and L1.

$\Delta\theta = \arcsin(|T|)$ $T = Uo \times U1$ where;
 T = a vector which is a cross-product of unit vectors Uo and U1.

Figure 6:
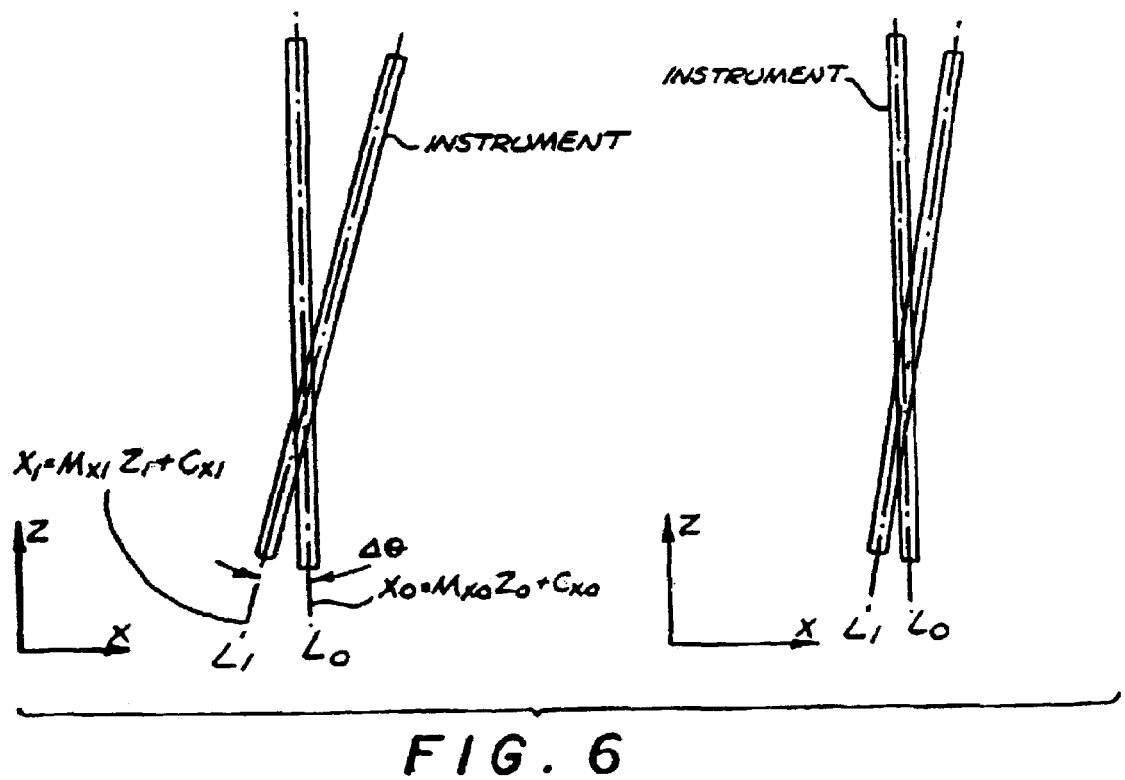
FIG. 6 is a schematic of the instrument moving about a pivot point.
Figure 9:
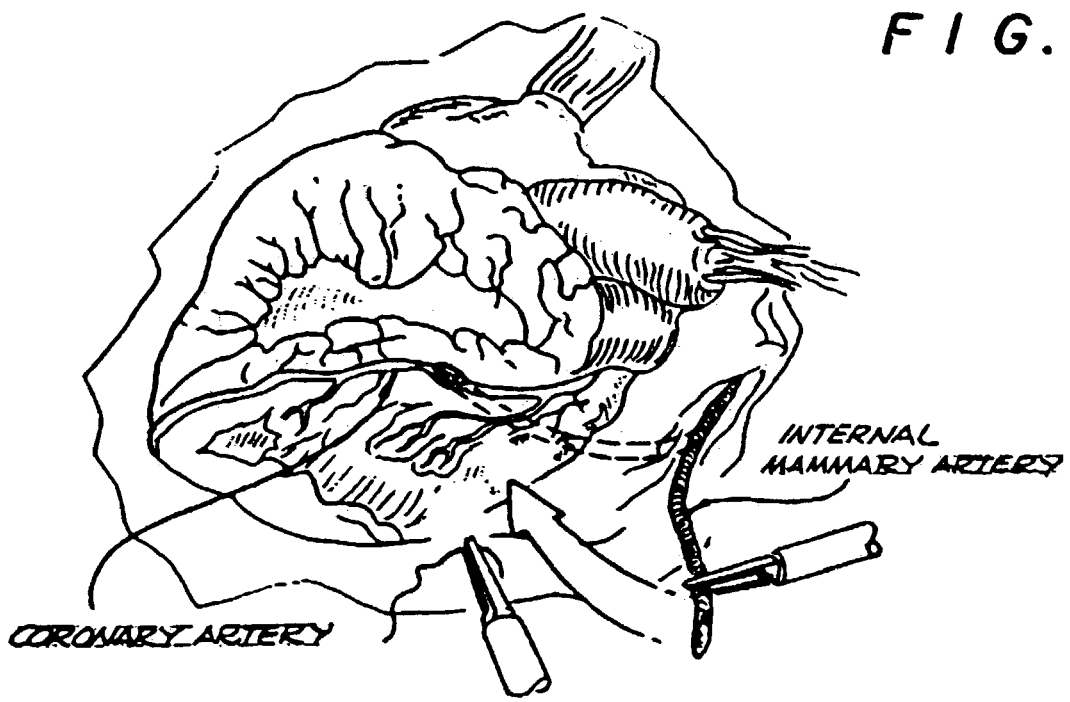
FIGS. 9-10A-I are illustrations showing an internal mammary artery being grafted to a coronary artery.

The unit vector of the new instrument position U1 is again determined using the positions sensors and the transformation matrix described above. If the angle $\Delta\theta$ is greater than a threshold value, then a new pivot point is calculated and Uo is set to U1. As shown in FIG. 6, the first and second instrument orientations can be defined by the line equations Lo and L1:

Lo:

$xo = M_x0 \cdot Zo + Cxo$ $yo = M_yo \cdot Zo + Cyo$

L1:

$x1 = Mx1 \cdot Z1 + Cx1$ $y1 = My1 \cdot Z1 + Cy1$ where;
 $Zo$ = a Z coordinate along the line Lo relative to the z axis of the first coordinate system.
 $Z1$ = a Z coordinate along the line L1 relative to the z axis of the first coordinate system.
 $Mxo$ = a slope of the line Lo as a function of Zo.
 $Myo$ = a slope of the line Lo as a function of Zo.
 $Mx1$ = a slope of the line L1 as a function of Z1.
 $My1$ = a slope of the line L1 as a function of Z1.
 $Cxo$ = a constant which represents the intersection of the line Lo and the x axis of the first coordinate system.
 $Cyo$ = a constant which represents the intersection of the line Lo and the y axis of the first coordinate system.
 $Cx1$ = a constant which represents the intersection of the L1 and the x axis of the first coordinate system.
 $Cy1$ = a constant which represents the intersection of the line L1 and the y axis of the first coordinate system.

The slopes are computed using the following algorithms:

$Mxo = Uxo/Uzo$ $Myo = Uyo/Uzo$ $Mx1 = Ux1/Uz1$ $My1 = Uy1/Uz1$ $Cx0 = Pox - Mx1 \cdot Poz$ $Cy0 = Poy - My1 \cdot Poz$ $Cx1 = P1x - Mx1 \cdot P1z$ $Cy1 = P1y - My1 \cdot P1z$ where;

Uo(x, y and z)=the unit vectors of the instrument in the first position within the first coordinate system.

U1(x, y and z)=the unit vectors of the instrument in the second position within the first coordinate system.

Po(x, y and z)=the coordinates of the intersection of the end effector and the instrument in the first position within the first coordinate system.

P1(x, y and z)=the coordinates of the intersection of the end effector and the instrument in the second position within the first coordinate system.

To find an approximate pivot point location, the pivot points of the instrument in the first orientation Lo (pivot point Ro) and in the second orientation L1 (pivot point R1) are determined, and the distance halfway between the two points Ro and R1 is computed and stored as the pivot point $R_{ave}$ of the instrument. The pivot point $R_{ave}$ is determined by using the cross-product vector T.

To find the points Ro and R1 the following equalities are set to define a line with the same orientation as the vector T that passes through both Lo and L1.

$$tx = Tx/Tz$$

$$ty = Ty/Tz$$

where;

tx=the slope of a line defined by vector T relative to the Z-x plane of the first coordinate system.

ty=the slope of a line defined by vector T relative to the Z-y plane of the first coordinate system.

Tx=the x component of the vector T.

Ty=the y component of the vector T.

Tz=the z component of the vector T.

Picking two points to determine the slopes Tx, Ty and Tz (eg. Tx=x1−xo, Ty=y1−yo and Tz=z1−z0) and substituting the line equations Lo and L1, provides a solution for the point coordinates for Ro (xo, yo, zo) and R1 (x1, y1, z1) as follows.

$$zo = ((Mx1-tx)z1 + Cx1 - Cxo)/(Mxo-tx)$$

$$z1 = ((Cy1-Cyo)(Mxo-tx)-(Cx1-Cxo)(Myo-ty))/\\((Myo-ty)(Mx1-tx)-(My1-ty)(Mxo-tx))$$

$$yo = Myo \cdot zo + Cyo$$

$$y1 = My1 \cdot z1 + Cy1$$

$$xo = Mxo \cdot zo + Cxo$$

$$x1 = Mx1 \cdot z1 + Cx1$$

The average distance between the pivot points Ro and R1 is computed with the following equation and stored as the pivot point of the instrument.

$$R_{ave} = ((x1+xo)/2, (y1+yo)/2, (z1+zo)/2)$$

The pivot point can be continually updated with the above described algorithm routine. Any movement of the pivot point can be compared to a threshold value and a warning signal can be issued or the robotic system can become disengaged if the pivot point moves beyond a set limit. The comparison with a set limit may be useful in determining whether the patient is being moved, or the instrument is being manipulated outside of the patient, situations which may result in injury to the patient or the occupants of the operating room.

To provide feedback to the surgeon the fingers of the instruments may have pressure sensors that sense the reacting force provided by the object being grasped by the end effector. Referring to FIG. 4, the controller 46 receives the pressure sensor signals Fs and generates corresponding signals Cm in block 78 that are provided to an actuator located within the handle. The actuator provides a corresponding pressure on the handle which is transmitted to the surgeon's hand. The pressure feedback allows the surgeon to sense the pressure being applied by the instrument. As an alternate embodiment, the handle may be coupled to the end effector fingers by a mechanical cable that directly transfers the grasping force of the fingers to the hands of the surgeon.

FIG. 7 shows a preferred embodiment of an end effector 80. The end effector 80 includes a tool 82 that is coupled to an arm 84 by a sterile coupler 86. The tool 82 has a first finger 88 that is pivotally connected to a second finger 90. The fingers can be manipulated to hold objects such as tissue or a suturing needle. The inner surface of the fingers may have a texture to increase the friction and grasping ability of the tool. The first finger 88 is coupled to a rod 92 that extends through a center channel 94 of the tool 82. The tool 82 may have an outer sleeve 96 which cooperates with a spring biased ball quick disconnect fastener 98 of the sterile coupler 86. The quick disconnect allows tools other than the finger grasper to be coupled to an arm. For example, the tool 82 may be decoupled from the coupler and replaced by a cutting tool. The coupler 86 allows the surgical instruments to be interchanged without having to re-sterilize the arm each time an instrument is plugged into the arm.

The sterile coupler 86 has a slot 100 that receives a pin 102 of the arm 84. The pin 102 locks the coupler 86 to the arm 84. The pin 102 can be released by depressing a spring biased lever 104. The sterile coupler 86 has a piston 106 that is attached to the tool rod and in abutment with an output piston 108 of a load cell 110 located within the arm 84.

The load cell 110 is mounted to a lead screw nut 112. The lead screw nut 112 is coupled to a lead screw 114 that extends from a gear box 116. The gear box 116 is driven by a reversible motor 118 that is coupled to an encoder 120. The entire arm 82 is rotated by a motor drive worm gear 122. In operation, the motor receives input commands from the controller 46 and activates, accordingly. The motor 118 rotates the lead screw 114 which moves the lead screw nut 112 and load cell 110 in a linear manner. Movement of the load cell 110 drives the coupler piston 106 and tool rod 92, which rotate the first finger 88. The load cell 110 senses the counteractive force being applied to the fingers and provides a corresponding feedback signal to the controller 46. The arm 84 may be covered with a sterile drape 124 so that the arm does not have to be sterilized after each surgical procedure.

FIGS. 8 and 8a show a preferred embodiment of a master handle assembly 130. The assembly 130 includes a master handle 132 that is coupled to an arm 134. The master handle 132 may be coupled to the arm 134 by a pin 136 that is inserted into a corresponding slot 138 in the handle 132. The handle 132 has a control button 140 that can be depressed by the surgeon. The control button 140 is coupled to a switch 142 by a shaft 144. The control button 140 corresponds to the input button 58 shown in FIG. 4, and activates the movement of the end effector.

The master handle 132 has a first gripper 146 that is pivotally connected to a second stationary gripper 148. Rotation of the first gripper 146 creates a corresponding linear movement of a handle shaft 150. The handle shaft 150 moves a gripper shaft 152 that is coupled a load cell 154 by a bearing 156. The load cell 154 senses the amount of pressure being applied thereto and provides an input signal to the controller 46. The controller 46 then provides an output signal to move the fingers of the end effector.

The load cell 154 is mounted to a lead screw nut 158 that is coupled to a lead screw 160. The lead screw 160 extends from a reduction box 162 that is coupled to a motor 164 which has an encoder 166. The controller 46 of the system receives the feedback signal of the load cell 110 in the end effector and provides a corresponding command signal to the motor to move the lead screw 160 and apply a pressure on the gripper so that the surgeon receives feedback relating to the force being applied by the end effector. In this manner the surgeon has a "feel" for operating the end effector.

The handle is attached to a swivel housing 168 that rotates about bearing 170. The swivel housing 168 is coupled to a position sensor 172 by a gear assembly 174. The position sensor 172 may be a potentiometer which provides feedback signals to the controller 46 that correspond to the relative position of the handle. The swivel movement is translated to a corresponding spin of the end effector by the controller and robotic arm.

The arm 134 may be coupled to a linear bearing 176 and corresponding position sensor 178 which allow and sense linear movement of the handle. The linear movement of the handle is translated into a corresponding linear movement of the end effector by the controller and robotic arm. The arm can pivot about bearings 180, and be sensed by position sensor 182 located in a stand 184. The stand 184 can rotate about bearing 186 which has a corresponding position sensor 188. The arm rotation is translated into corresponding pivot movement of the end effector by the controller and robotic arm.

A human hand will have a natural tremor typically resonating between 6-12 hertz. To eliminate tracking movement of the surgical instruments with the hand tremor, the system may have a filter that filters out any movement of the handles that occurs within the tremor frequency bandwidth. Referring to FIG. 4, the filter 184 may filter analog signals provided by the potentiometers in a frequency range between 6-12 hertz.

As shown in FIGS. 9 and 10A-I, the system is preferably used to perform a cardiac procedure such as a coronary artery bypass graft (CABG). The procedure is performed by initially cutting three incisions in the patient and inserting the surgical instruments 22 and 24, and the endoscope 26 through the incisions. One of the surgical instruments 22 holds a suturing needle and accompanying thread when inserted into the chest cavity of the patient. If the artery is to be grafted with a secondary vessel, such as a saphenous vein, the other surgical instrument 24 may hold the vein while the end effector of the instrument is inserted into the patient.

The internal mammary artery (IMA) may be severed and moved by one of the instruments to a graft location of the coronary artery. The coronary artery is severed to create an opening in the artery wall of a size that corresponds to the diameter of the IMA. The incision(s) may be performed by a cutting tool that is coupled to one of the end effectors and remotely manipulated through a master handle. The arteries are clamped to prevent a blood flow from the severed mammary and coronary arteries. The surgeon manipulates the handle to move the IMA adjacent to the opening of the coronary artery. Although grafting of the IMA is shown and described, it is to be understood that another vessel such as a severed saphaneous vein may be grafted to bypass a blockage in the coronary artery.

Figure 10A:
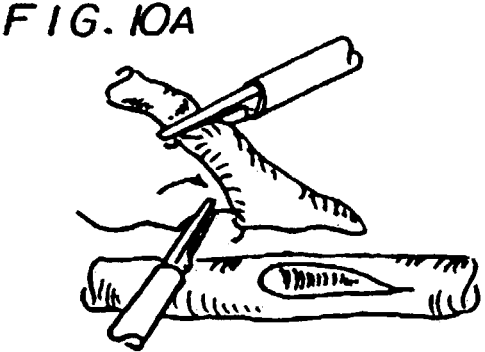
Figure 10B:
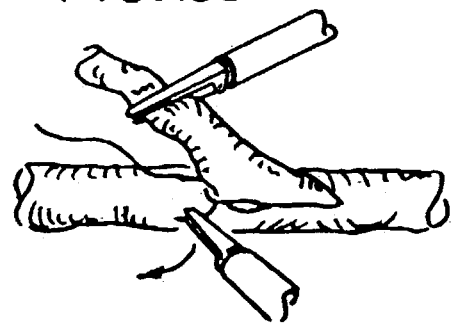
Figure 10C:
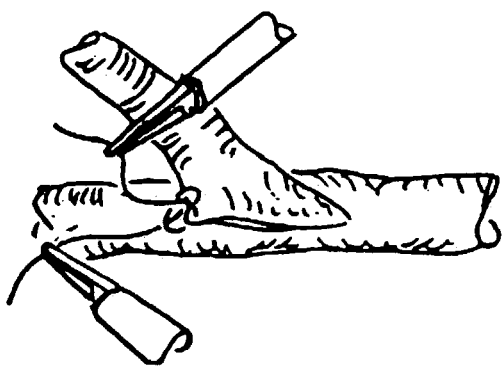
Figure 10D:
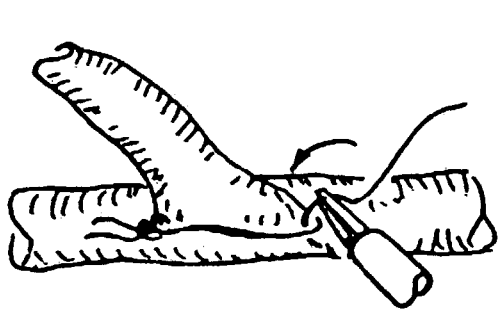
Figure 10E:
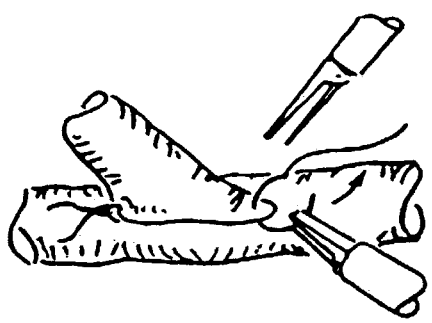
Figure 10F:
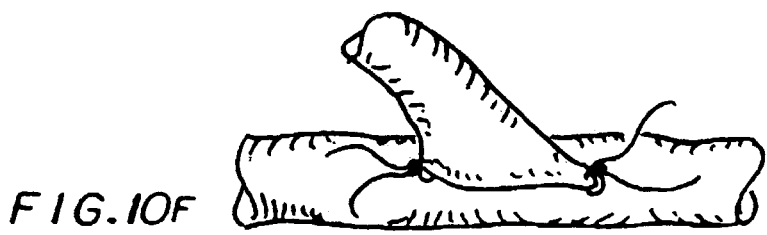
Figure 10G:
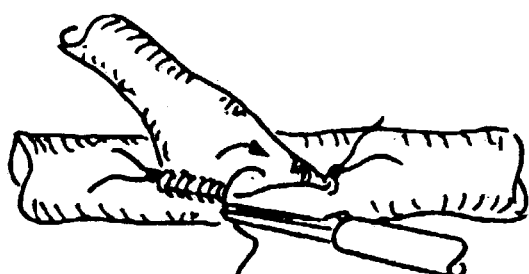
Figure 10H:
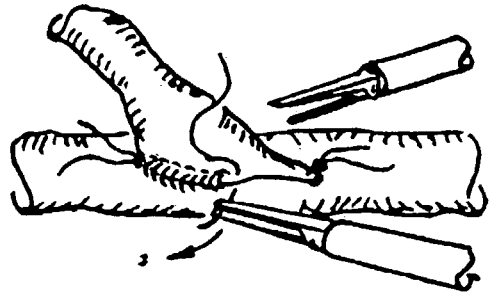
Figure 10I:
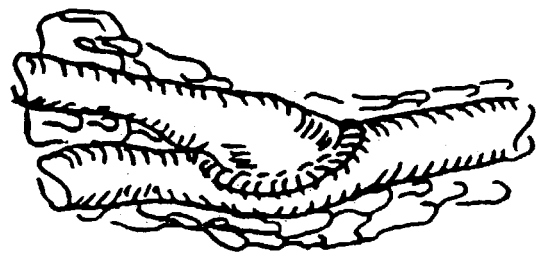

Referring to FIGS. 10A-10I, the surgeon moves the handle to manipulate the instrument into driving the needle through the IMA and the coronary artery. The surgeon then moves the surgical instrument to grab and pull the needle through the coronary and graft artery as shown in FIG. 10B. As shown in FIG. 10C, the surgical instruments are then manipulated to tie a suture at the heel of the graft artery. The needle can then be removed from the chest cavity. As shown in FIGS. 10D-F, a new needle and thread can be inserted into the chest cavity to suture the toe of the graft artery to the coronary artery. As shown in FIGS. 10H-I, new needles can be inserted and the surgeon manipulates the handles to create running sutures from the heel to the toe, and from the toe to the heel. The scaled motion of the surgical instrument allows the surgeon to accurately move the sutures about the chest cavity. Although a specific graft sequence has been shown and described, it is to be understood that the arteries can be grafted with other techniques. In general the system of the present invention may be used to perform any minimally invasive anastomostic procedure.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A medical robotic system that utilizes an endoscope, comprising:
    a first robotic arm;
    a first surgical instrument coupled to said first robotic arm;
    a second robotic arm;
    a second surgical instrument coupled to said second robotic arm;
    a third robotic arm coupled to the endoscope, the third robotic arm including a plurality of linkages and a plurality of motors, wherein the plurality of linkages are coupled together and movable by selective actuation of the plurality of motors so as to be capable of moving the endoscope in a three-dimensional space;
    a plurality of handles coupled to said first and second robotic arms; and
    a foot pedal coupled to said third robotic arm and the endoscope, and operable by an operator to move said third robotic arm and the endosdope by selective actuation of the plurality of motors.

2. The system of claim 1, further comprising a cabinet, said handles being connected to said cabinet.

3. The system of claim 1, wherein said first and second robotic arms move in conjunction with movement of said handles.

4. The system of claim 3, further comprising an input device that can functionally disconnect said handles from said first and second robotic arms.

5. A medical robotic system that utilizes an endoscope, comprising:
    a first robotic arm,
    a first surgical instrument coupled to said first robotic arm;
    a second robotic arm;
    a second surgical instrument coupled to said second robotic arm;
    a third robotic arm coupled to the endoscope, the third robotic arm including a plurality of linkages and a plurality of motors, wherein the plurality of linkages are coupled together and movable by selective actuation of the plurality of motors so as to be capable of moving the endoscope in a three-dimensional space;
    a plurality of handles coupled to said first and second robotic arms; and input means for causing said third robotic arm to be moved according to input generated from sensed movement of a foot of a system operator by selective actuation of the plurality of motors.

6. The system of claim 5, further comprising a cabinet, said handles being connected to said cabinet.

7. The system of claim 5, wherein said first and second robotic arms move in conjunction with movement of said handles.

8. The system of claim 7, further comprising an input device that can functionally disconnect said handles from said first and second robotic arms.

9. A method for operating a medical robotic system comprising:
 causing a surgical instrument to be moved during a minimally invasive surgical procedure in response to an input received from a handle;
 receiving a camera view from an endoscope of a surgical site at which the minimally invasive surgical procedure is being performed; and
 causing the endoscope to be repositioned during the minimally invasive surgical procedure in response to an input received from a foot pedal by selective actuation of a plurality of motors in a robotic arm coupled to the endoscope so as to move the endoscope in a three-dimensional space.

10. A medical robotic system that utilizes an endoscope, comprising:
 a first robotic arm;
 a first surgical instrument coupled to the first robotic arm;
 a second robotic arm including a plurality of coupled together linkages and a plurality of motors;
 an endoscope coupled to the second robotic arm so as to be movable in a three-dimensional space by selective actuation of the plurality of motors;
 a first handle coupled to the first robotic arm and operable by an operator for manipulating the first surgical instrument; and
 a foot pedal coupled to the second robotic arm and operable by the operator for positioning the endoscope by selective actuation of the plurality of motors.

11. The system of claim 10, wherein said foot pedal includes a button that can be depressed to actuate said second robotic arm.

12. The system of claim 10, further comprising a third robotic arm, and a second surgical instrument coupled to the third robotic arm.

13. The system of claim 12, further comprising a second handle coupled to the third robotic arm and operable by the operator for manipulating the second surgical instrument.

14. A medical robotic system that utilizes an endoscope, comprising:
 a first robotic arm;
 a first surgical instrument coupled to the first robotic arm;
 a second robotic arm including a plurality of coupled together linkages and a plurality of motors;
 an endoscope coupled to the second robotic arm so as to be movable in a three-dimensional space by selective actuation of the plurality of motors;
 handle means for causing the first surgical instrument to be manipulated according to a first input generated from sensed movement of a hand of a surgeon; and
 input means for causing the endoscope to be positioned according to a second input generated from sensed movement of a foot of the surgeon by selective actuation of the plurality of motors.

15. The system of claim 14, wherein said input means includes a foot pedal.

16. The system of claim 15, wherein said foot pedal includes a button that can be depressed to activate said second robotic arm.

17. The system of claim 14, further comprising a third robotic arm and a second surgical instrument coupled to said third robotic arm.

18. The system of claim 17, wherein said handle means is positioned to be manipulatable by another hand of the surgeon for manipulating the second surgical instrument.

* * * * *